(12) United States Patent
Kreiss et al.

(10) Patent No.: US 7,695,900 B2
(45) Date of Patent: Apr. 13, 2010

(54) METHOD AND DEVICE FOR DETECTING BIOLOGICALLY ACTIVE SUBSTANCES

(75) Inventors: Wolfgang Kreiss, Bergisch Gladbach (DE); Guenther Eberz, Odenthal-Holz (DE); Hans-Georg Rast, Odenthal (DE); Claus Weisemann, Apex, NC (US)

(73) Assignee: Bayer Aktiengesellschaft, Leverkusen (DE)

( * ) Notice: Subject to any disclaimer, the term of this patent is extended or adjusted under 35 U.S.C. 154(b) by 388 days.

(21) Appl. No.: 11/711,560

(22) Filed: Feb. 27, 2007

(65) Prior Publication Data

US 2007/0154978 A1 Jul. 5, 2007

Related U.S. Application Data

(62) Division of application No. 10/424,067, filed on Apr. 25, 2003, now Pat. No. 7,183,113.

(60) Provisional application No. 60/386,045, filed on Jun. 5, 2002.

(51) Int. Cl.
 *C12Q 1/00* (2006.01)
 *C12Q 1/66* (2006.01)
(52) U.S. Cl. .............................. 435/4; 435/8
(58) Field of Classification Search ........................ None
 See application file for complete search history.

(56) References Cited

U.S. PATENT DOCUMENTS

| 4,371,615 A | 2/1983 | Miwa et al. |
| 5,591,872 A | 1/1997 | Pearson et al. |
| 6,017,722 A | 1/2000 | Becvar et al. |
| 6,340,572 B1 | 1/2002 | Becvar |

FOREIGN PATENT DOCUMENTS

| WO | WO 92/18614 | 10/1992 |
| WO | WO 01/32911 | 5/2001 |
| WO | WO 01/85664 | 11/2001 |

OTHER PUBLICATIONS

Chem. Abstr. 1989:510414 Caplus. Jungblut, et al., Improvement in the reproducibility of the luminescent bacteria toxicity test by addition of external aldehyde, Zeitschrift fuer Angewandte Zoologie, 75(3), 317-23 (1988).
Weins, et al., Toxicological evaluation of harmful Substances by in situ enzymatic and biological detection in high-performance thin-layer chromatography, J. Chromatography A 750, 403-407 (1996).

*Primary Examiner*—Mark Navarro
(74) *Attorney, Agent, or Firm*—Edwards Angell Palmer & Dodge LLP; Gabriel J. McCool; Barry Kramer

(57) ABSTRACT

This application claims a method for detecting biologically active substances, comprising the following steps
 a) providing a support carrying substances to be tested
 b) providing a suspension containing luminescent microorganisms,
 c) coating the support with the suspension of microorganisms,
 d) detecting the biologically active substances on the support by detecting the change in luminescence of the suspension of microorganisms, and
 e) stimulating the luminescence of the microorganisms before or during detection, and/or
 f) extending the period of luminescence of the microorganisms by employing substances for regulating and extending the period of luminescence of the microorganisms.

15 Claims, 2 Drawing Sheets

METHOD AND DEVICE FOR DETECTING BIOLOGICALLY ACTIVE SUBSTANCES

Figure 1:
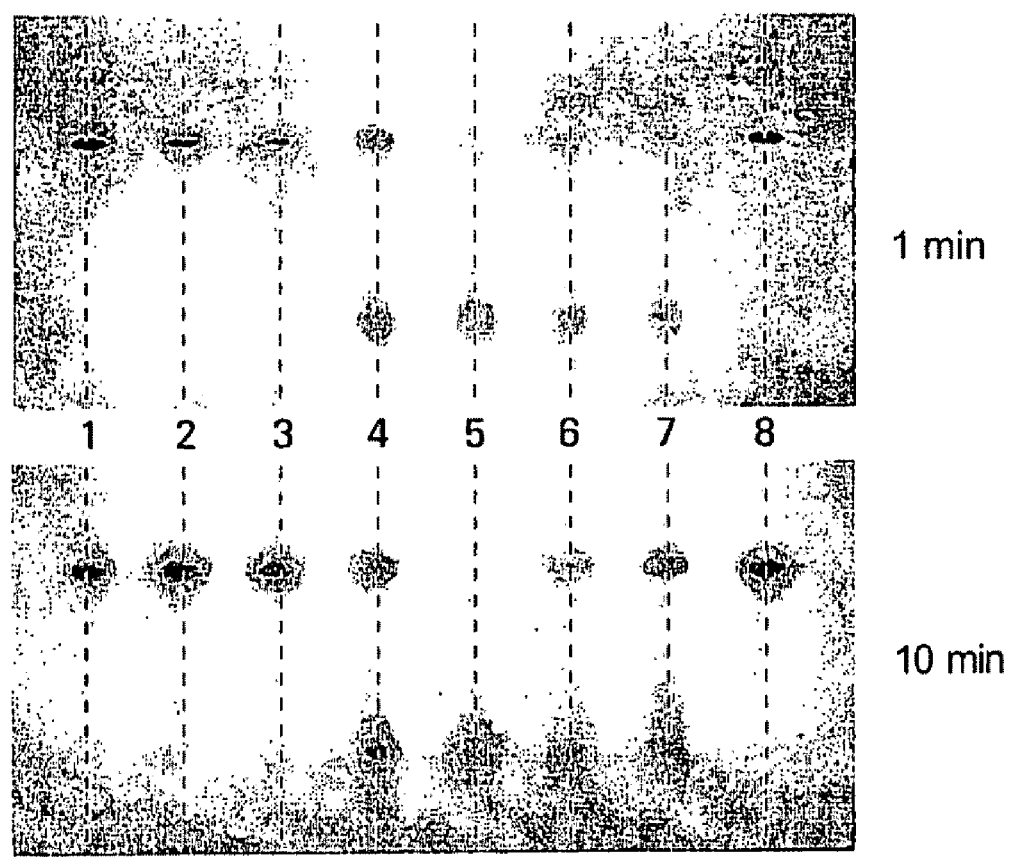

Luminescence assays have gained general importance for studying the biological activity of substances and are used, for example, in eco-toxicological applications or in the screening of test substances of pharmaceutical research. The assay methods are based on substances directly influencing bioluminescent processes and indicate a biological effect or toxicity by a change in luminescence intensity. In this connection, toxic substance properties are frequently detected by a reduction in bioluminescence, while specific biological actions are normally recorded selectively by stimulation of reporter gene systems based on bioluminescence.

A widely applied method for determining toxicity utilizes the reduction in luminescence of luminescent bacteria in the presence of toxic substances. According to this method, the substance to be tested is added to a suspension of luminescent bacteria. Toxic substances reduce the luminescence intensity and can be recorded in this way [A. A. Bulich, Bioluminescence Assays, pp. 57-74 in G. Bitton and B. J. Dutka, Toxicity Testing Using Microoganisms, Vol. 1, 1986, CRC Press, Boca Raton]. For complex substance mixtures which are frequently present in real samples this assay method provides merely summary results and does not allow any conclusions to be drawn about the active component. In addition, the simultaneous presence of toxic substances (reduction in luminescence) and compounds stimulating luminescence result in false evaluations of such samples.

In order to assess safely the biological activity of mixtures, these mixtures must be split into individual components which then have to be individually tested. A direct method for this is based on coupling bioluminescence with chromatographic separation techniques (chromatographic detection of effects). In this connection, substance mixtures are separated by thin-layer chromatography and toxic substances are detected via the reduction in luminescence by coating the thin-layer chromatography plate with luminescent bacteria [U.S. Pat. No. 6,017,722; U.S. Pat. No. 6,340,572; U.S. Pat. No. 6,238,928; G. Eberz, H.-G. Rast, K. Burger, W. Kreiss, C. Weisemann, *Chromatographia* 43, 5 (1996)].

The, in principle, powerful chromatographic detection of effects according to the prior art has been unable up to now to gain broad acceptance in practice, since successful application requires at the same time know-how in analytical techniques and microbiology and correspondingly extensive laboratory equipment.

In addition to the chromatographic separation of substances, the detection step must be provided with a sufficient amount of a fresh culture containing vital luminescent bacteria. The luminescence detection carried out according to the prior art provides only low luminescence on the thin-layer chromatography plate so that detection is possible only with great expense, for example via very highly sensitive imaging systems with residual light amplification.

The kit described in U.S. Pat. No. 6,340,572 provides for applying a diluent to the bioluminescent agent, i.e. two components and a dilution step are conceived there for preparing the detecting agent.

The method described in U.S. Pat. No. 6,017,722 has the limitation described therein regarding the duration of bioluminescence on the chromatographic medium. This limitation results from evaporation processes which impair the vitality of the microorganisms.

In the case of *Vibrio harveyi*, it is known that borate diesters increase luminescence [X. Chen, S. Schauder, N. Potier, A. van Dorsselaer, I. Pelczer, B. L. Bassler, F. M. Hughson, Nature, Vol. 415, 545, 2002]. Furthermore, it is known that N-acylhomoserine lactones are suitable which stimulate bioluminescence in *Vibrio fischeri* as bacterial signalling substances [J. Throup, M. K. Winson, N. J. Bainton, B. W. Bycroft, G. S. A. B. Stewart; Proceedings of the 8$^{th}$ International Symposium of Bioluminescence and Chemiluminescence, Cambridge 1994, pp. 89-92, John Wiley].

Coating the plate using a spraying technique, described in U.S. Pat. No. 6,017,722, has numerous disadvantages in practice. Using apparatuses common in the laboratory, it is not possible to achieve a uniform coating of the surface. This is clearly verified by the examples given in U.S. Pat. No. 6,017,722. A portion of the bacteria is harmed by evaporation processes during the spraying process so that only reduced luminescence yields are achieved. In addition, for reasons of occupational health and safety, the formation of aerosols is to be avoided when working with microorganisms, i.e. coating by spraying with living bacteria requires an effective suction device.

It is an object of the invention to provide a method and a kit for detecting biologically active substances that overcomes the limitations of the prior art for the practical use of the chromatographic detection of effects and provides, even at a low concentration of the microorganisms, a luminescence emission which is sufficiently stable for detection and long-lasting.

The object of the invention is achieved by a method for detecting biologically active substances, comprising the steps:

a) providing a support carrying substances to be tested b) providing a suspension containing luminescent microorganisms, c) coating the support with the suspension of microorganisms, d) detecting the biologically active substances on the support by detecting the change in luminescence of the suspension of microorganisms, characterized in that e) the luminescence of the microorganisms is stimulated before or during detection, and/or f) the period of luminescence of the microorganisms is extended by substances for regulating and extending the period of luminescence of the microorganisms.

In order to increase the luminescence power of the suspension of microorganisms used, the method of the invention uses substances which specifically stimulate bioluminescence. Luminescence-stimulating substances which may be used are N-acylhomoserine lactones such as N-(3-oxohexanoyl)-L-homoserine lactone, dipeptides, oligopeptides, boron compounds such as borate diesters or quinolones or biochemical precursors of luminescence-inducing substances.

Normally, biological effects show a distinct time dependence. Using the method of the invention, acutely toxic effects of antibiotic effects which occur only after a relatively long incubation time can be distinguished well. In order to study the said time dependence, a sufficient luminescence stability on the support over the observation period is required. For regulation and extension, i.e. the time-related stabilization of bioluminescence, it is possible to use substances which prevent, for example, the microorganism-coated support from drying out rapidly. Suitable for this purpose are in particular oligomers and polymers, in particular biocompatible and hydrophilic ones, for example based on polysaccharides. Preference is given to using for this acrylates, polyvinylpyridines, polyethylene glycols, polyether derivatives, polysaccharides, dextrans, modified celluloses, peptides and proteins, particularly preferably in a concentration of up to 2% of the medium containing them.

The solution for cultivating the suspension of microorganisms may contain the substances stimulating the luminescence of the microorganisms or components for regulating and extending the period of luminescence of the microorganisms.

Suspensions of microorganisms may be obtained from freeze-dried microorganisms or frozen cell concentrates by reconstitution using a reconstitution medium. For the rapid reconstitution of freeze-dried microorganisms or microorganisms concentrated by centrifugation, stimulation of the luminescence or regulation and extension of the period of luminescence of the microorganisms by adding appropriate substances to the dilution medium or to the reconstitution medium is particularly advantageous, since without stimulation only low luminescence intensities or short luminescence periods are attained.

When diluting suspensions of microorganisms with inducer-containing media, it is likewise advantageous to add to the dilution medium substances for stimulating or extending luminescence. Thus, relatively low amounts of luminescent microorganisms are required without having to suffer losses in the quality of luminescence detection so that the provision becomes less complicated.

An increase in luminescence may furthermore be achieved by a high cell density of more than $2*10^9$ cells/ml in the suspension of microorganisms, for example by adding to the medium for cultivating the microorganisms amino acids or other carboxylic acids, in particular aspartic acid.

Examples of luminescent microorganisms which may be used are the luminescent marine bacteria *Vibrio fischeri*. Furthermore, other luminescent microorganisms such as, for example, *Vibrio harveyi, Photobacterium leiognathi, Photobacterium phosphoreum, Photorhabdus luminescens* are also suitable. In addition, it is also possible to use genetically modified luminescent microorganisms.

The support carrying the biologically active substances may be a thin-layer chromatography plate or an electrophoresis gel or another, preferably planar, separation system on which the biologically active substances are present in the form of zones. The biologically active substances may also be present in the form of spots of a substance array on a support.

The luminescence of the suspension of microorganisms may be detected by photographic methods or imaging techniques.

The support may be coated by immersing the support in a suspension of microorganisms. During the immersion process, the luminescent microorganisms are accumulated on the surface to be coated. Thus it is possible, for example, to dilute the *Vibrio fischeri* suspension from an overnight culture to more than five times the volume, while still achieving reliable detection of toxic substances, for example on a thin-layer plate coated with silica gel. This effect is surprising, since from the pH of the immersion suspension (approx. pH 7) a negative charge of the silica-gel matrix and, at the same time, a negative surface charge of the luminescent bacteria must be assumed. One possible explanation for this unexpected behaviour is provided by other interactions compensating for the electrostatic forces and by a reduced negative charge density for the bacterial envelope. Measurements of the zeta potential of *Vibrio fischeri* in the immersion solution support this assumption.

Moreover, the support is coated more rapidly by immersing, thus resulting in the possibility of time-dependent measurements even after short exposure times. In this manner it is possible to detect acute toxic effects even within a few seconds. Furthermore, high-quality fractionation of substances on the support is retained, since there is hardly any diffusion of the substance zones during this short period.

The support is preferably coated homogeneously, leading to a uniform background and an improved signal-to-noise ratio during luminescence measurement.

Depending on the biological system used, the biological activity may cause both a reduction and an increase in luminescence. The time course of inhibition or stimulation of the luminescence of the suspension of microorganisms can be recorded and analysed under one measurement regime.

The luminescence intensity of the microorganisms can be further increased and, as a result, the detection sensitivity for the detection can be improved by cooling the microorganisms or by irradiating the microorganisms with light.

The invention furthermore relates to a kit for carrying out detection of effects in a simple manner, which may contain the following components:

microorganisms in a form stabilized for transport and storage, one or more cultivation media or recipes for cultivation media or the individual components of cultivation media for the microorganisms, additives for stimulating the growth and/or luminescence of microorganisms or the biochemical precursors thereof and/or additives for extending the period of luminescence of microorganisms.

The microorganisms may be stabilized by freeze-drying or by freezing with suitable preservatives or by adsorption to suitable porous support materials or by inclusion in gel-like materials.

The kit may furthermore contain an immersion chamber for homogenous coating of a support with the microorganisms. Such an immersion chamber preferably has a cooling jacket or heat exchanger for cooling the suspension of microorganisms.

Applying an immersion chamber to the coating step increases the luminescence of the bacteria surface and leads to uniform coating. The uniform background resulting from the coating quality allows a reliable detection of substance zones.

The application of the method of the invention within a quality assurance system normally requires information regarding calibration, validation and monitoring of testing means. For these tasks, a test support which provides the required information in one step was conceived as component of the kit of the invention. The test support has defined amounts of a reference substance with known biological action. The quality check or calibration can be carried out by simple immersion of the test support in the suspension of luminescent microorganisms to be tested and subsequent measurements using an imaging system.

In a preferred embodiment, the test support consists of a strip of paper, glass, a polymeric material or metal, which contains spots of the reference substances applied to it in a defined manner. The test support is particularly preferably coated with porous materials such as silica gel.

If the reference substance used is, for example, 4-nitrophenol or a copper salt, the test result revealed by the imaging system is dark zones at the positions of the spots of the reference substances. Thus the function of both the microbiological kit and the imaging system required for the actual measurement can be validated.

As an option for laboratories or other test environments without microbiological equipment, the kit of the invention contains a device for simplified cultivation of microorganisms. In a preferred embodiment, this device consists of a glass or plastic container whose design ensures good oxygen exchange with the cultivation suspension and contains a magnetic stirring bar and is optionally already filled with a cultivation solution and/or a dilution medium and/or a reconstitution medium. After inoculating with microorganisms, this container is placed at room temperature on a magnetic stirrer set to a low stirring speed. In this way it is possible to prepare, on the basis of the method of the invention, overnight cultures by using conventional laboratory apparatuses, without additional apparatuses such as, for example, temperature-controlled shaker tables being required for cultivation.

In the kit of the invention, the cultivation medium may contain substances, substance mixtures or solutions thereof or the biochemical precursors thereof as additive, which stimulate growth and/or luminescence of the microorganisms.

In one embodiment, the cultivation media contain dipeptides, oligopeptides, boron compounds, quinolones or N-acylhomoserine lactones or the biochemical precursors thereof. In a preferred embodiments, the bioluminescence of *Vibrio fischeri* is stimulated by using N-(3-oxohexanoyl)-L-homoserine lactone and/or boron compounds.

In a further embodiment, cultivation media are used which contain, in addition to the usual components for the cultivation of microorganisms, amino acids or carboxylic acids at concentrations of up to 2%. In another embodiment, *Vibrio fischeri* are cultivated in a medium which contains between 10 mg/l and 500 mg/l aspartic acid. Using such cultivation media, it is possible to achieve very high cell densities in overnight cultures.

The cultivation media may also contain additives which regulate and extend bioluminescence. Such additives may be oligomers or polymers or else acrylates, polyvinylpyridines, polyethylene glycols, polyether derivatives, polysaccharides, dextrans, modified celluloses, peptides and proteins.

As an alternative or at the same time, a dilution medium, contained in the kit, for diluting the suspension of microorganisms or reconstitution medium for preparing ready-to-use suspensions of microorganisms from cell concentrates or stabilized preparations of microorganisms may contain growth- and/or luminescence-stimulating additives or the biochemical precursors thereof such as N-acylhomoserine lactones, dipeptides, oligopeptides, boron compounds or quinolones.

The dilution and/or reconstitution medium may also contain additives which regulate and extend luminescence, such as oligomers or polymers, acrylates, polyvinylpyridines, polyethylene glycols, polyether derivatives, polysaccharides, dextrans, modified celluloses, peptides and proteins.

In a preferred embodiments, the dilution and/or reconstitution medium for stimulating *Vibrio fischeri* luminescence contain N-(3-oxohexanoyl)-L-homoserine lactone and/or boron compounds.

The kit of the invention may furthermore contain a light source and/or a means for cooling the suspension of microorganisms. It may additionally contain a device for fractionating samples by means of planar separation techniques such as, for example, thin-layer chromatography or gel electrophoresis.

Moreover, work protocols for the individual steps in the preparation of the suspension of microorganisms and in the luminescence measurement and/or information on application examples may be enclosed in the kit.

The method of the invention and the kit enable a high detection sensitivity even at a low concentration of microorganisms and overall achieve a highly economical method.

Due to special cultivation methods, specific stimulation of bioluminescence and the possible accumulation in the immersion step, the method of the invention achieves a particularly high performance and, due to its robustness, allows for a particularly simple embodiment.

The kit of the invention represents a substantial advance compared to the prior art, since it enables investigation laboratories to apply the method of the invention in practice, without microbiological know-how and equipment for microbiological work being required there. A high robustness of the measurement is achieved by the specific increase in bioluminescence. In addition, the complicated accumulation of luminescent microorganisms, for example by centrifugation, can be dispensed with.

The high luminescent power even allows a substantial dilution of the detection medium.

In order to increase the luminescence when diluting overnight cultures or reconstituting bacteria which, for example, have been made storable by freeze-drying or freezing, the kit contains media with suitable additives or recipes for such media.

In addition, an immersion chamber enables rapid coating and thus permits studying biological effects which start very rapidly. At the same time, fractionation of the substance zones, for example on a thin-layer plate, is essentially retained during this rapid detection, since only short diffusion times are possible here. Another advantage of the immersion chamber is in occupational hygiene, since, in contrast to spraying techniques, no aerosols of microorganisms are produced.

FIGURES AND EXAMPLES

The figures show:

FIG. 1 luminescence images of a TLC plate, 1 min and 10 min after incubation with a bacterial suspension.

FIG. 2 luminescence detection using a bacterial suspension prepared without and with addition of aspartic acid to the cultivation medium.

Example 1

According to the method of the invention, Example 1 shows the specific detection of substances changing the luminescence of microorganisms, using the kit of the invention.

The luminescence change was detected by coating a thin-layer chromatography (TLC) plate on which a mixture had been separated by means of the AMD technique [Ref.: K. Burger, *Chemistry of Plant Protection*, 12, 181-195 (1995)] with *Vibrio fischeri* by immersing the TLC support in a *Vibrio fischeri* suspension.

Reaction product mixtures which contained the bacteriotoxic component 4-tert-butylphenol and also fractions from a work-up process in which the concentration of 4-tert-butylphenol was to be reduced were studied. These samples were classified by the following application scheme:

1: 30 ng of 4-tert-butylphenol reference
2: 1 µl of reaction product 1
3: 1 µl of reaction product 2
4: 100 µl of preparation A of reaction product 1
5: 100 pl of preparation B of reaction product 1
6: 100 µl of preparation C of reaction product 1
7: 100 µl of preparation D of reaction product 1
8: 30 ng of 4-tert-butylphenol reference Preparation of the *Vibrio fischeri* Immersion Suspension:

An Erlenmeyer flask containing 400 ml of cultivation medium was inoculated with bacteria from a *Vibrio fischeri* strain stock. The inoculated cultivation solution is then incubated in a shaker incubator at 28° C. overnight.

The cultivation medium contained:

| | |
|---|---|
| 30 g/l | NaCl |
| 6.1 g/l | $NaH_2PO_4 \cdot H_2O$ |
| 2.75 g/l | $K_2HPO_4 \cdot 3H_2O$ |
| 0.204 g/l | $MgSO_4 \cdot 7H_2O$ |
| 0.5 g/l | $(NH4)_2HPO_4$ |
| 5 g/l | Peptone from caseine (Merck) |
| 0.5 g/l | Yeast extract (DIFCO) |
| 3 ml/l | Glycerol | and was adjusted to pH 7.2±0.2 with the aid of 1 N HCl or 1 N NaOH. The medium was autoclaved prior to use at 121° C. for 20 min.

Luminescence Detection:

The bacteria suspension was introduced into a CAMAG immersion chamber for thin-layer chromatography. The thin-layer plate was coated by immersing it in the bacterial suspension for a few seconds. Luminescence images were taken of the coated plate in the wet state using the Nightowl camera system (EG&G Berthold). The fluorescence image was analysed visually on the display of the video imaging system (FIG. 1). For documentation, TIFF files were formatted and labelled using suitable graphic programs (Adobe Photoshop, MS Powerpoint).

Result:

FIG. 1 depicts the result of the luminescence detection after 1 min and 10 min incubation time. In the bioluminescence detection, the bacteriotoxic substances are indicated by bioluminescence quenching. In each case 30 ng of 4-tert-butylphenol had been applied to TLC lanes 1 and 8. This corresponds approximately to the proportion of 4-tert-butylphenol in the reaction products 1 and 2 (lanes 2 and 3). The preparations A to D (lanes 4-7) which had been applied in a 100-fold amount had a distinctly reduced proportion of 4-tert-butylphenol. With the large amount applied, further traces of luminescence-quenching substances became visible. Comparison of the luminescence images after 1 min and after 10 min incubation on the TLC plate resulted in an additional active component for lane 6, which was no longer visible after a longer incubation time. Apparently, a substance was present here, which impairs the vitality of the bacterial cells only briefly. The rapid luminescence detection according to the method of the invention thus provides information about different actions of mixture components and, in addition, maintains the initial resolution of the thin-layer chromatographic separation. The zone broadening due to diffusion is already apparent when comparing the two luminescence images which are 9 min apart.

Example 2

According to the method of the invention, Example 2 shows the increase in luminescence due to improved growth with the addition of aspartic acid to the cultivation medium.

Figure 2A:
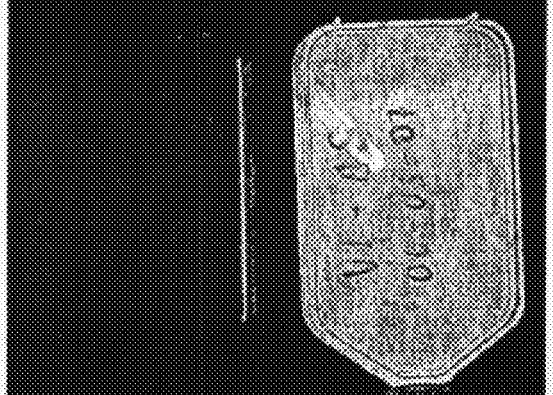
Figure 2B:
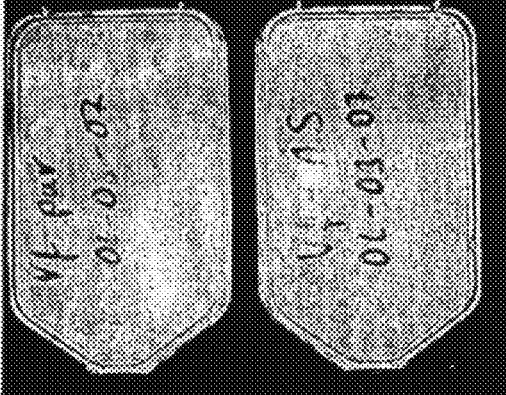

In two cultivation experiments carried out in parallel, bacterial suspensions were prepared according to the method described below. In order to test the influence of aspartic acid, 12.5 mg of aspartic acid had been added to the cultivation medium of one of the two reaction mixtures. The effect of the addition of aspartic acid was detected by taking luminescence images using the Nightowl camera system from EG&G Berthold and is depicted in FIGS. 2a and 2b. In the present case, the reaction mixture admixed with aspartic acid showed a distinct luminescence already after 18 h of incubation (right cultivation vessel in FIG. 2a), while bioluminescence starts in the aspartic acid-free medium only at a later time (FIG. 2b).

Cultivation Method for *Vibrio fischeri:*

A tissue culture flask (e.g. Falcon Cat. No. 353110) which contains 125 ml of cultivation medium and a magnetic stirring bar was inoculated with bacteria from a *Vibrio fischeri* strain stock. The inoculated cultivation solution was then incubated with slow stirring on a magnetic stirrer at room temperature.

The invention claimed is:

1. A method for detecting a biologically active substance, comprising the steps of:
   a) providing a planar separation system carrying biologically active substances to be tested,
   b) coating the planar separation system with a suspension of luminescent *Vibrio fischeri* bacteria that have been cultured in a growth medium comprising between 10 mg/l and 500 mg/l aspartic acid, the suspension further comprising a luminescence-stimulating additive for extending the period of luminescence of the luminescent bacteria, said additive being selected from the group consisting of a N-acylhomoserine lactone, a dipeptide, a oligopeptide, a boron compound, and a quinolone, and
   c) allowing said bacteria to react with said biologically active substances;
   d) measuring the luminescence of the suspension of bacteria, wherein a change in luminescence, relative to the luminescence measured in the absence of a biologically active substance, identifies the tested substance to be a biologically active substance.

2. The method according to claim 1, wherein said suspension of luminescent *Vibrio fischeri* bacteria is prepared from freeze-dried bacteria or frozen cell concentrates.

3. The method according to claim 1, wherein the luminescence-stimulating additive is N-(3-oxohexanoyl)-L-homoserine lactone.

4. The method according to claim 1, wherein cell density of the suspension of luminescent *Vibrio fischer* bacteria is $2 \times 10^9$ cells/ml.

5. The method according to claim 1, wherein the planar separation system on which the biologically active substances have been separated is selected from the group consisting of a thin layer-chromatography plate, an electrophoresis gel, an array or a planar separation system on which the biologically active substances are present in the form of zones.

6. The method according to claim 1, wherein the planar separation system is an array.

7. The method according to claim 1, wherein the planar separation system is coated homogeneously with the suspension of luminescent bacteria.

8. The method according to claim 1, wherein the planar separation system is coated with the suspension of luminescent *Vibrio fischeri* bacteria by immersing the planar separation system in the suspension of luminescent *Vibrio fischeri* bacteria.

9. The method according to claim 8, wherein immersing causes accumulation of the *Vibrio fischeri* bacteria on the surface of the planar separation system.

10. The method according to claim 1, wherein measuring the luminescence of the suspension of luminescent *Vibrio fischeri* bacteria is achieved by photographic methods or imaging techniques.

11. The method according to claim 1, wherein the time course of inhibition or stimulation of the luminescence of the suspension of luminescent *Vibrio fischeri* bacteria is recorded and analysed.

12. The method according to claim 11, wherein the suspension of luminescent *Vibrio fischeri* bacteria is subjected to cooling prior to and/or during the measuring of the luminescence.

13. The method according to claim 12, wherein the suspension of luminescent *Vibrio fischeri* bacteria is subjected to irradiation with light prior to and/or during the measuring of the luminescence.

14. The method of claim 1 wherein the boron compound is a borate diester.

15. The method according to claim 1, wherein the growth medium used to culture the luminescent *Vibrio fischeri* bacteria comprises 2% w/v of aspartic acid.

* * * * *